United States Patent [19]

Kanter et al.

[11] Patent Number: 5,028,705
[45] Date of Patent: Jul. 2, 1991

[54] PREPARATION OF PYRAZOLO[5,1-B]QUINAZOLONES

[75] Inventors: Hartmut Kanter, Ludwigshafen; Burkhard Ort, Wachenheim, both of Fed. Rep. of Germany

[73] Assignee: BASF Aktiengesellschaft, Ludwigshafen, Fed. Rep. of Germany

[21] Appl. No.: 242,118

[22] Filed: Sep. 9, 1988

[30] Foreign Application Priority Data

Sep. 11, 1987 [DE] Fed. Rep. of Germany ....... 3730536

[51] Int. Cl.$^5$ .......................................... C07D 487/02
[52] U.S. Cl. ................................................... 544/250
[58] Field of Search ........................................ 544/250

[56] References Cited

U.S. PATENT DOCUMENTS

| | | | |
|---|---|---|---|
| 3,883,524 | 5/1975 | Wolf et al. | 544/252 X |
| 4,247,555 | 1/1981 | Sircar et al. | 544/250 X |
| 4,261,996 | 4/1981 | Sircar et al. | 544/250 X |
| 4,261,997 | 4/1981 | Sircar et al. | 544/250 X |
| 4,303,795 | 12/1981 | Conley et al. | 544/250 X |
| 4,925,946 | 5/1990 | Kanter et al. | 544/250 |

FOREIGN PATENT DOCUMENTS 1242863  8/1971  United Kingdom ................ 544/250

OTHER PUBLICATIONS

Angew. Chem. vol. 74, pp. 839–847 Jahrg. 1962, Nr. 21 Synthesen Und Reaktionen Neuer Ortho ... Menzel, et al.
Journal of Heterocyclic Chemistry vol. 18, 1981 pp. 117–121 Reactions of 2H-3,1Benzoxazine-2,4–(1H)Dione ... Sircar, et al.
Journal of Medicinal Chemistry, vol. 24, 1981, pp. 735–742 Pyrazolo[5,1-b]Quinazolin-9-Ones: ... Sircar, et al.
Spath, et al., Chemische Berichte, vol. 68, pp. 2221–2226 (1935).
Enomoto, et al., Chemical Abstracts, vol. 75; 95588u (1971).

*Primary Examiner*—Diana Rivers
*Attorney, Agent, or Firm*—Oblon, Spivak, McClelland, Maier & Neustadt

[57] ABSTRACT

Pyrazolo[5,1-b]quinazolones are prepared by reacting isatoic anhydrides with pyrazolones at from 100° to 180° C. in an inert organic solvent with simultaneous azeotropic removal of the water formed in the course of the reaction.

12 Claims, No Drawings

PREPARATION OF PYRAZOLO[5,1-b]QUINAZOLONES

BACKGROUND OF THE INVENTION

1. Field of the Invention

The present invention relates to a novel process for preparing pyrazolo[5,1-b]quinazolones by reacting isatoic anhydrides with pyrazolones in an inert organic solvent at from 100° C. to 180° C. with simultaneous azeotropic removal of the water formed in the course of the reaction.

2. Discussion of the Background

It is known to prepare 2-methylpyrazolo[5,1-b]quinazolone by reacting isatoic anhydride with 3-methylpyrazol-5-one in the melt or in a high-boiling solvent at from 200° C. to 250° C. (Angew. Chem. 74 (1962), 839).

J. Heterocycl. Chem. 18 (1981), 117 and J. Med. Chem. 24 (1981), 735 disclose the preparation of further pyrazolo[5,1-b]quinazolones. The starting materials used are likewise isatoic anhydrides and pyrazolones. This reaction takes place in N,N-dimethylformamide as solvent in the presence of sodium hydride as base at from −10° C. to 0° C.

Neither procedure is easy to carry out on an industrial scale. On the one hand, special measures are required in order to be able to perform the reaction at a very high temperature in a melt or in a high-boiling solvent; on the other hand, the use of sodium hydride as a base is not without its problems and necessitates a great deal of attention to safety.

SUMMARY OF THE INVENTION

It is an object of the present invention to provide a new process for preparing pyrazolo[5,1-b]quinazolones which starts from industrially readily accessible starting materials and which should give the target products in good yield without recourse to extraordinary technical resources.

We have found that this object is achieved with a process for preparing a pyrazolo[5,1-b]quinazolone of the formula I

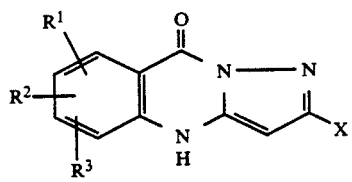

where $R^1$, $R^2$ and $R^3$ are identical or different and each is independently of the others hydrogen, halogen, $C_1$-$C_4$-alkoxy, nitro, $C_1$-$C_4$-alkyl, trifluoromethyl, carboxyl, cyano, carbamoyl, $C_1$-$C_4$-monoalkyl- or -dialkyl-carbamoyl, phenylcarbamoyl, sulfamoyl, $C_1$-$C_4$-monoalkyl- or -dialkylsulfamoyl, phenylsulfamoyl, hydroxysulfonyl or $C_1$-$C_4$-alkanoylamino and X is $C_1$-$C_4$-alkyl or substituted or unsubstituted phenyl, by reacting an isatoic anhydride of the formula II

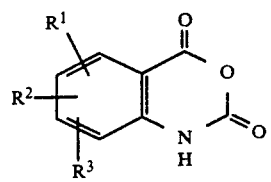

where $R^2$, $R^2$ and $R^3$ are each as defined above, with a pyrazolone of the formula III

where X is as defined above, which comprises performing the reaction at from 100° C. to 180° C. in an inert organic solvent with simultaneous azeotropic removal of the water formed in the course of the reaction.

DETAILED DESCRIPTION OF THE PREFERRED EMBODIMENTS

All the alkyls appearing in the abovementioned formulae may be, not only straight-chain, but also branched.

Where substituted phenyl appears in the formulae I or III, suitable substituents are for example $C_1$-$C_4$-alkyl, $C_1$-$C_4$-alkoxy, halogen, in particular fluorine, chlorine or bromine, nitro and cyano.

$R^1$, $R^2$, $R^3$ and X are each for example methyl, ethyl, propyl, isopropyl, butyl, isobutyl or sec-butyl.

X is further for example phenyl, 2-methylphenyl, 4-methylphenyl, 4-ethylphenyl, 4-propylphenyl, 4-isopropylphenyl, 2,4-dimethylphenyl, 2-methoxyphenyl, 4-ethoxyphenyl, 4-isopropoxyphenyl, 4-butoxyphenyl, 2,6-dimethoxyphenyl, 4-fluorophenyl, 4-chlorophenyl, 4-bromophenyl, 2,4-dichlorophenyl, 2- or 3-nitrophenyl or 3- or 4-cyanophenyl.

$R^1$, $R^2$ and $R^3$ are each further for example fluorine, chlorine, bromine, methoxy, ethoxy, propoxy, isopropoxy, butoxy, isobutoxy, sec-butoxy, monomethylcarbamoyl, dimethylcarbamoyl, monoethylcarbamoyl, diethylcarbamoyl, monopropylcarbamoyl, dipropylcarbamoyl, monoisopropylcarbamoyl, diisopropylcarbamoyl, monobutylcarbamoyl, dibutylcarbamoyl, N-methyl-N-ethylcarbamoyl, monomethylsulfamoyl, dimethylsulfamoyl, monoethylsulfamoyl, diethylsulfamoyl, monopropylsulfamoyl, dipropylsulfamoyl, monoisopropylsulfamoyl, diisopropylsulfamoyl, monobutylsulfamoyl, dibutylsulfamoyl, N-methyl-N-ethylsulfamoyl, formylamino, acetylamino, propionylamino, butyrylamino or isobutyrylamino.

The process according to the invention is preferred for those pyrazolo[5,1-b]quinazolones of the formula I where X is methyl or phenyl and $R^1$, $R^2$ and $R^3$ are each hydrogen, nitro, methoxy, phenylsulfamoyl, chlorine or bromine.

The process according to the invention is carried out in an inert organic solvent at from 100° C. to 180° C., preferably at from 120° C. to 160° C.

In general, atmospheric pressure is employed. In some cases, however, it may also be of advantage to carry out the reaction under superatmospheric pressure (from 0 up to 5 bar gauge).

A suitable inert organic solvent is in particular xylene, dichlorobenzene, nitrobenzene or methyl benzoate.

In general this solvent is used in an amount of from 3 to 10 parts by weight per part by weight of isatoic anhydride II.

Isatoic anhydride II and pyrazolone III are customarily used in a molar ratio of from 1.2:1 to 0.8:1.

It is also possible to perform the process according to the invention in the presence of 1 to 50 percent by weight, preferably 5 to 30 percent by weight and particularly 10 to 20 percent by weight, based in each case on the pyrazolone of the formula III, of anhydrous sodium carbonate or potassium carbonate.

Advantageously, the novel process is carried out by introducing inert solvent and pyrazolone III initially, heating with stirring to the temperature according to the invention and adding isatoic anhydride II. After the evolution of carbon dioxide has ceased, the reaction mixture may be admixed with catalyst and is in general stirred at the temperature according to the invention for from 1 to 10 hours, during which the water formed in the course of the reaction is azeotropically distilled out of the reaction mixture, the function of entrainer being performed by the inert solvent. Isatoic anhydride II and pyrazolone III may also be used as an aqueous paste, in which case the water is azeotropically distilled out of the reaction mixture together with the water of reaction.

The amount of solvent distilled off during the reaction may be recycled into the reaction mixture in the form of fresh or regenerated solvent.

On completion of the reaction, which proceeds via a ring-opened intermediate of the formula IV

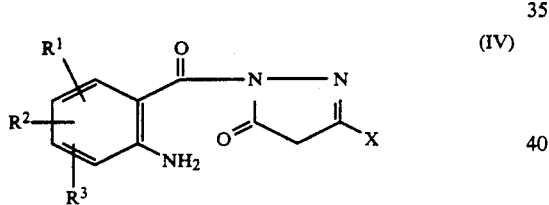

where $R^1$, $R^2$, $R^3$ and X are each as defined above, the resulting pyrazolo[5,1-b]quinazolone of the formula I is separated off, washed with the particular solvent, methanol and warm water and dried.

It is also possible to remove the solvent by steam distillation and to isolate the pyrazolo [5,1-b]-quinazolone from an aqueous suspension. In this alternative, impurities go into solution at above pH 7 and thus can be removed in the course of filtration.

Using the process according to the invention, which may be carried out not only continuously but also batchwise, the pyrazolo[5,1-b]quinazolones can be obtained in good yields without recourse to extraordinary technical resources and the solvent used in this synthesis may in general be reused following regeneration (distillation).

Pyrazolo[5,1-b]quinazolones are useful intermediates for the synthesis of dyes and pigments.

The Examples which follow serve to illustrate the invention in more detail.

EXAMPLE 1

100 g of 3-methylpyrazol-5-one were introduced in 1,000 g of xylene. After heating to 115° C., 200 g of 5-chloroisatoic anhydride were slowly added to the mixture. After $CO_2$ evolution had subsided, the mixture was stirred for 20 minutes, then heated to 140° C. and maintained at that temperature until no further water of reaction distilled off. This is followed by cooling down to 70° C., filtration, washing first with 550 g of methanol and then with warm water, and drying to leave 200 g of a colorless powder of the formula

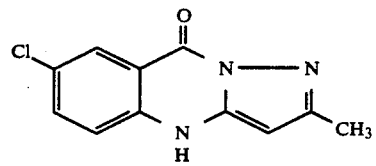

EXAMPLE 2

160 g of 3-phenylpyrazol-5-one were added to 750 g of xylene and heated to 115° C. 160 g of isatoic anhydride were then slowly added to the mixture. After $CO_2$ evolution had ceased, the mixture was stirred for 20 minutes, heated to 140° C. and maintained at that temperature for 6 hours. It was then cooled down to 95° C. and diluted with 1,000 ml of water, and the solvent was distilled off by steam distillation. Thereafter it was diluted with 2,000 ml of water, admixed with 40 g of 50% strength by weight sodium hydroxide solution and subsequently stirred for 1 hour. This was followed by filtration, washing neutral with water and drying to leave 220 g of a yellowish powder of the formula

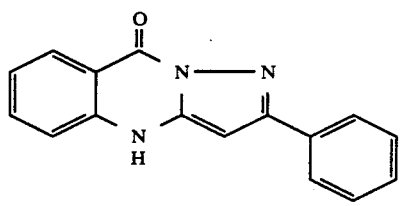

EXAMPLE 3

100 g of 3-methylpyrazol-5-one and 200 g of 6-chloroisatoic anhydride were heated in 700 g of nitrobenzene at 150° C. for 4 hours. The reaction mixture was then cooled down to 80° C. and filtered. The filter residue was washed with 500 g of methanol and then with 3,000 ml of warm water and dried to leave 195 g of a colorless powder of the formula

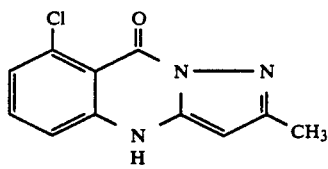

EXAMPLE 4

50 g of 3-methylpyrazol-5-one were introduced in 350 g of xylene and heated to 115° C. At that temperature 80 g of isatoic anhydride were slowly added and stirred in until the evolution of $CO_2$ had ceased. 10 g of anhydrous sodium carbonate were then added, and the mixture was heated to 135° C. and stirred until no further water of reaction passed over. The mixture was cooled down to 100° C., 200 ml of water were added, and xylene was driven off by means of steam. Thereafter the aqueous suspension was cooled down to 70° C. and brought to a pH of from 7 to 7.5 with 5 g of 96% strength by weight sulfuric acid. The mixture was then filtered, and the filter residue was washed with warm water until the run-off was colorless, and dried to leave 85 g of a product of the formula

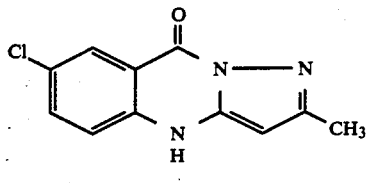

EXAMPLE 5

100 g of 3-methylpyrazol-5-one and 200 g of 4-chloroisatoic anhydride were heated in 800 g of dichlorobenzene at 155° C. for 3 hours. After cooling down to 80° C., the mixture was filtered, and the filter residue was washed with 500 g of methanol and then with 3,000 ml of warm water and dried to leave 180 g of a colorless powder of the formula

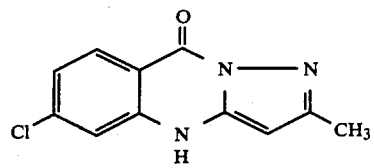

EXAMPLE 6

200 g of 3-methylpyrazol-5-one were introduced in 1,500 g of methyl benzoate, heated with stirring to 115° C. and then slowly admixed with 300 g of 3, 5-dichloroisatoic anhydride. The reaction mixture was then stirred at 170° C. for 3 hours while the water of reaction was distilled off. After cooling to 90° C, the reaction mixture was filtered, and the filter residue was washed with 1,000 g of methanol and 3,000 ml of warm water and dried to leave 250 g of a light-colored powder of the formula

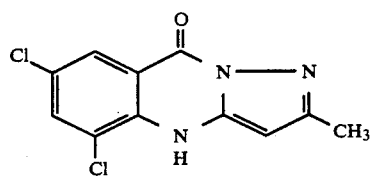

The compounds listed in the Table below with reaction conditions and yield were obtained in a similar manner.

| Example No. | Formula | Solvent | Temp. [°C.] | Yield [%] |
| --- | --- | --- | --- | --- |
| 7 | ![structure] | nitrobenzene | 160 | 73 |
| 8 | ![structure] | nitrobenzene | 165 | 85 |
| 9 | ![structure] | dichlorobenzene | 170 | 82 |
| 10 | ![structure] | nitrobenzene | 170 | 84 |

-continued
| Example No. | Formula | Solvent | Temp. [°C.] | Yield [%] |
|---|---|---|---|---|
| 11 | 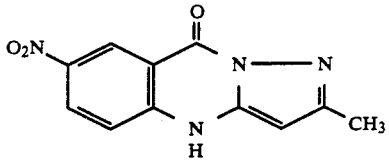 | methyl benzoate | 160 | 75 |
| 12 | 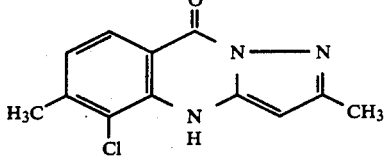 | nitrobenzene | 160 | 78 |
| 13 | 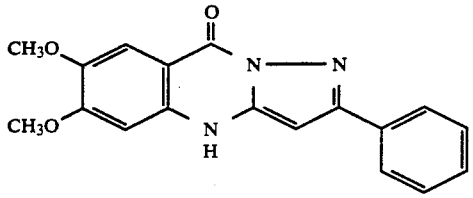 | nitrobenzene | 160 | 84 |
| 14 | 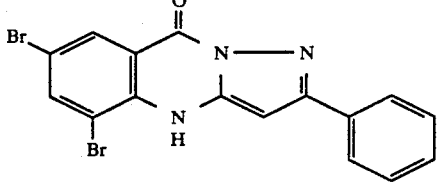 | methyl benzoate | 160 | 89 |
| 15 | 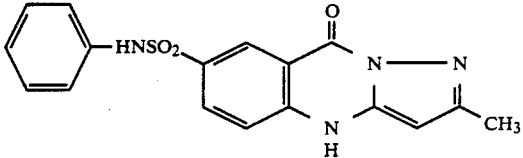 | xylene | 140 | 87 |
| 16 | 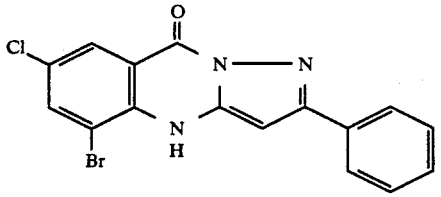 | nitrobenzene | 170 | 83 |
| 17 | 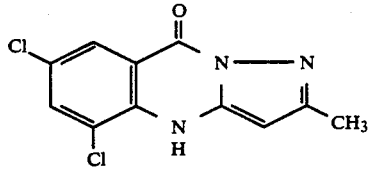 | nitrobenzene | 170 | 85 |
| 18 | 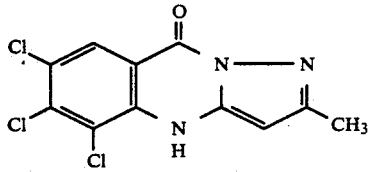 | nitrobenzene | 170 | 75 |
We claim:
1. A process for preparing a pyrazolo[5,1-b]quinazolone of the formula I

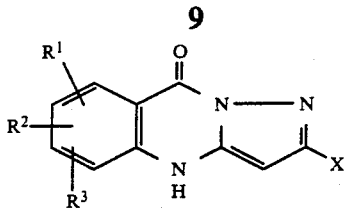

where $R^1$, $R^2$ and $R^3$ are identical or different and each is independently of the others hydrogen, halogen, $C_1$-$C_4$-alkoxy, nitro, $C_1$-$C_4$-alkyl, trifluoromethyl, carboxyl, cyano, carbamoyl, $C_1$-$C_4$-monoalkyl- or -dialkyl-carbamoyl, phenylcarbamoyl, sulfamoyl, $C_1$-$C_4$-monoalkyl- or -dialkylsulfamoyl, phenylsulfamoyl, hydroxysulfonyl or $C_1$-$C_4$-alkanoylamino and X is $C_1$-$C_4$-alkyl or substituted or unsubstituted phenyl, by reacting an isatoic anhydride of the formula II

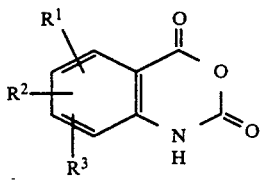

where $R^1$, $R^2$ and $R^3$ are each as defined above, with a pyrazolone of the formula III

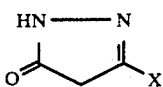

where X is as defined above, which comprises performing the reaction at from 100° C. to 180° C. in an inert organic solvent with simultaneous azeotropic removal of the water formed in the course of the reaction.

2. A process as claimed in claim 1, wherein the reaction is carried out in the presence of a catalytic amount of anhydrous sodium carbonate or potassium carbonate.

3. A process as claimed in claim 1, wherein the reaction is carried out in xylene, dichlorobenzene, nitrobenzene or methyl benzoate as solvent.

4. The process of claim 1, wherein said substituted phenyl is phenyl substituted by $C_{1-4}$ alkyl, $C_{1-4}$ alkoxy, halogen, nitro or cyano.

5. The process of claim 1, wherein said substituted phenyl is phenyl substituted by fluorine, chlorine or bromine.

6. The process of claim 1, wherein $R^1$, $R^2$, $R^3$ or X is methyl, ethyl, propyl, isopropyl, butyl, isobutyl or sec-butyl.

7. The process of claim 1, where X is phenyl, 2-methylphenyl, 4-methylphenyl, 4-ethylphenyl, 4-propylphenyl, 4-isopropylphenyl, 2,4-dimethylphenyl, 2-methoxyphenyl, 4-ethoxyphenyl, 4-isopropoxyphenyl, 4-butoxyphenyl, 2,6-dimethoxyphenyl, 4-fluorophenyl, 4-chlorophenyl, 4-bromophenyl, 2,4-dichlorophenyl, 2- or 3-nitrophenyl or 3- or 4-cyanophenyl.

8. The process of claim 1, wherein $R^1$, $R^2$ or $R^3$ is fluorine, chlorine, bromine, methoxy, ethoxy, propoxy, iropropoxy, butoxy, isobutoxy, sec-butoxy, monomethylcarbamoyl, dimethylcarbamoyl, monoethylcarbamoyl, diethylcarbamoyl, monopropylcarbamoyl, dipropylcarbamoyl, monoisopropylcarbamoyl, diisopropylcarbamoyl, monobutylcarbamoyl, dibutylcarbamoyl, N-methyl-N-carbamoyl, monomethylsulfamoyl, dimethylsulfamoyl, monethylsulfamoyl, diethylsulfamoyl, monopropylsulfamoyl, dipropylsulfamoyl, monoisopropylsulfamoyl, diisopropylsulfamoyl, monobutylsulfamoyl, dibutylsulfamoyl, N-methylethylsulfamoyl, formylamino, acetylamino, propionylamino, butyrylamino or isobutyrylamino.

9. The process of claim 1, wherein X is methyl or phenyl and $R^1$, $R^2$ and $R^3$ are each independently hydrogen, nitro, methoxy, phenylsulfamoyl, chlorine or bromine.

10. The process of claim 1, comprising performing said reaction at a temperature of from 120° C. to 160° C.

11. The process of claim 3, wherein said solvent is used in an amount of from 3 to 10 parts by weight of solvent per part by weight of said isatoic anhydride of formula (II).

12. The process of claim 1, wherein said isatoic anhydride of formula (II) and said pyrazolone of formula (III) are used in a molar ratio of from 1.2:1 to 0.8:1.

* * * * *